US009266110B2

(12) United States Patent
Su et al.

(10) Patent No.: US 9,266,110 B2
(45) Date of Patent: Feb. 23, 2016

(54) REACTION TUBE FOR PERFORMING ISOTHERMAL POLYMERASE CHAIN REACTION THEREIN

(71) Applicant: GeneReach Biotechnology Corp., Taichung (TW)

(72) Inventors: Chen Su, Taichung (TW); Ping-Hua Teng, Taichung (TW)

(73) Assignee: GeneReach Biotechnology Corp., Taichung (TW)

( * ) Notice: Subject to any disclaimer, the term of this patent is extended or adjusted under 35 U.S.C. 154(b) by 348 days.

(21) Appl. No.: 13/846,833

(22) Filed: Mar. 18, 2013

(65) Prior Publication Data

US 2013/0217112 A1 Aug. 22, 2013

Related U.S. Application Data

(63) Continuation-in-part of application No. 13/013,831, filed on Jan. 26, 2011, now abandoned.

(30) Foreign Application Priority Data

Oct. 14, 2010 (TW) ............................ 099135105 A

(51) Int. Cl.

| | |
|---|---|
| ***C12M 1/24*** | (2006.01) |
| ***C12M 3/00*** | (2006.01) |
| ***B01L 7/00*** | (2006.01) |

(Continued)

(52) U.S. Cl.

CPC ................. *B01L 7/52* (2013.01); *B01L 3/5082* (2013.01); *B01L 7/54* (2013.01); *B01L 9/065* (2013.01); *B01L 2300/0858* (2013.01); *B01L 2300/16* (2013.01); *B01L 2300/1827* (2013.01)

(58) Field of Classification Search

CPC ......... B01L 3/5082; B01L 7/52; B01L 9/065; B01L 2300/16; B01L 2300/1805

See application file for complete search history.

(56) References Cited

U.S. PATENT DOCUMENTS

| | | | | |
|---|---|---|---|---|
| 5,273,907 A * | 12/1993 | Malmquist | .................... | 436/165 |
| 5,827,480 A | 10/1998 | Haff et al. | | |
| 6,068,978 A * | 5/2000 | Zaun et al. | .................. | 435/6.16 |

(Continued)

OTHER PUBLICATIONS

Chang et al., A thermally baffled device for highly stabilized convective PCR., Biotechnol. J. Jan. 2012.

(Continued)

*Primary Examiner* — Michael Hobbs
(74) *Attorney, Agent, or Firm* — CKC & Partners Co., Ltd.

(57) ABSTRACT

A reaction tube for performing isothermal polymerase chain reaction therein is provided and includes an upper section, a lower capillary section, a linkage connecting the upper section and the lower capillary section, and a thermal conductor. The lower capillary section has an annealing portion, an annular heating groove, and a close end. The annealing portion is connected with the linkage, and the annular heating groove is connected with the annealing portion. The close end is connected with the annular heating groove. The thermal conductor tightly embraces the annular heating groove of the lower capillary section for conducting heat. Accordingly, a heat generated from the heating source will conduct to the annular heating groove of the lower capillary section of the reaction tube, a temperature gradient along the reaction tube is then provided in order to perform a thermal convection, thereby performing the isothermal polymerase chain reaction in the reaction tube.

13 Claims, 5 Drawing Sheets

(51) Int. Cl.
*B01L 3/00* (2006.01)
*B01L 9/06* (2006.01)

(56) References Cited

U.S. PATENT DOCUMENTS

| | | | |
|---|---|---|---|
| 6,312,886 B1 | 11/2001 | Lee et al. | |
| 7,238,321 B2 | 7/2007 | Wittwer et al. | |
| 7,273,749 B1 | 9/2007 | Wittwer et al. | |
| 2008/0206751 A1* | 8/2008 | Squirrell et al. | 435/6 |

OTHER PUBLICATIONS

Tsai et al., Detection of white spot syndrome virus by polymerase chain reaction performed under insulated isothermal conditions, Journal of Virological Methods. 131(2012) 134-137. Feb. 2012.

Tsai et al., Development of TaqMan Probe-Based Insulated Isothermal PCR (iiPCR) for Sensitive and Specific On-Site Pathogen Detection, PLOS One. vol. 7, issue 9 pp. 1-10. Sep. 2012.

* cited by examiner

REACTION TUBE FOR PERFORMING ISOTHERMAL POLYMERASE CHAIN REACTION THEREIN

RELATED APPLICATIONS

This application is a continuation-in-part of U.S. patent application Ser. No. 13/013,831, filed Jan. 26, 2011, which claims priority to Taiwan Application Serial Number 99135105, filed Oct. 14, 2010, all of which are herein incorporated by reference.

BACKGROUND

1. Technical Field

The present disclosure relates to a container for performing nucleic acid amplification reaction therein. More particularly, the present disclosure relates to a reaction tube for performing isothermal polymerase chain reaction therein.

2. Description of Related Art

The nucleic acid amplification reaction is a scientific technique in molecular biology to amplify a single or a few copies of a particular deoxyribonucleic acid (DNA) sequence by repeating the same procedure with particular polymerases. The common techniques such as polymerase chain reaction (PCR), reverse transcription polymerase chain reaction (RT-PCR), and real-time polymerase chain reaction (real-time PCR) all belong to nucleic acid amplification reaction techniques.

The PCR is majorly used to amplify a particular DNA, whereas the RT-PCR is used to reverse transcribing a specified RNA fragment to a particular DNA fragment followed by amplifying the particular DNA fragment, namely complementary DNA (cDNA). The real-time PCR, also called quantitative PCR, is used to amplify and quantify a targeted DNA simultaneously, where the main reagents associated in this procedure are fluorescent probe and dyes. Taking all together, the principle of the nucleic acid amplification reactions mentioned above is PCR.

Furthermore, some skills presented lately also belong to nucleic acid amplification reactions, such as rolling circle amplification (RCA), loop mediated amplification (LAMP), nucleic acid sequence based amplification (NASBA), and three way junction (TWJ).

Regarding to general PCR, the initialization step is used for mixing and heating DNA templates, primers, and a buffer solution to the reaction temperature about 90° C. for disrupting the hydrogen bonds between two single-stranded DNA templates, namely the denaturation step. The second step is used for cooling the reaction temperature to about 50° C. for annealing the primers and the single-stranded DNA template. The final step is used for holding the temperature at about 70° C. for extending the primers. The particular DNA is copied by repeating the above procedure.

The types of the apparatus for the nucleic acid amplification reaction are classified according to the prices. The cheaper type includes a container, such as a tube or a capillary, and two heaters. The two heaters are respectively disposed on the two ends of the container. One heater heats the container to about 90° C., and the other heats the container to about 50° C. The solution convection in the container takes place because of the density difference of the solution at the two ends of the container, wherein the density difference is caused by the temperature difference between the two ends. The DNA and the primers is circulated through the container and heated from 90° C. to 50° C. circularly for performing the nucleic acid amplification reaction.

The heater is made of a metal block. The block has a groove for receiving the end of the container, and the shape of the groove is designed to be fitted to the end of the container. However, the groove does not completely match with the container; it implies that the groove remains some protrusions and indentations when the end of the container is received by the groove. Therefore, the edge of the protrusions and the indentations do not completely and evenly contact to the container in order to conduct heat to the container. Thus, the container cannot be heated evenly. The reaction efficiency of the nucleic acid amplification reaction will be reduced.

SUMMARY

According to an embodiment of the present disclosure, a reaction tube for performing an isothermal polymerase chain reaction therein includes an upper section for receiving a reagent, a lower capillary section, a linkage connecting the upper section and the lower capillary section, and a thermal conductor. The lower capillary section has an annealing portion, an annular heating groove, and a close end. The annealing portion is connected with the linkage, and the annular heating groove is connected with the annealing portion. The close end is connected with the annular heating groove. The thermal conductor tightly embraces the annular heating groove of the lower capillary section for conducting heat to the lower capillary section evenly from a heating source, where the thermal conductor is received by the annular heating groove. Moreover, an outer diameter of the annealing portion is greater than an outer diameter of the annular heating groove. Accordingly, while loading reagents required for performing polymerase chain reaction in the reaction tube, and disposing the reaction tube on the heating source, the heat generated by the heat source will be evenly conducted to a specific region around the annular heating groove of the reaction tube via the thermal conductor of the present disclosure, then a temperature gradient along the reaction tube can be provided in order to perform a thermal convection, thereby performing an efficient isothermal polymerase chain reaction in the reaction tube.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawings.

Figure 1:
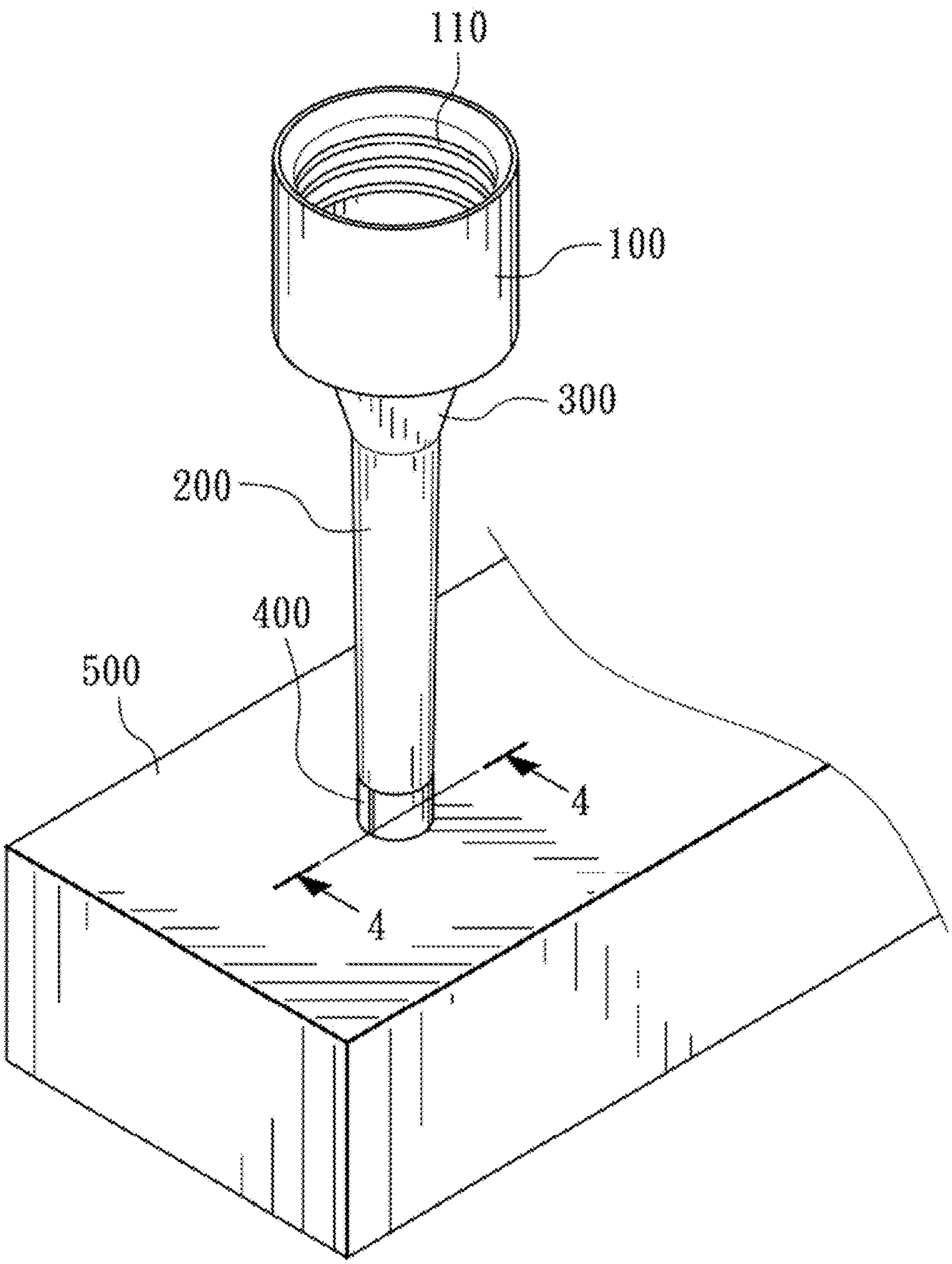
FIG. 1 is a perspective view of a reaction tube according to an embodiment of the present disclosure.
Figure 2:
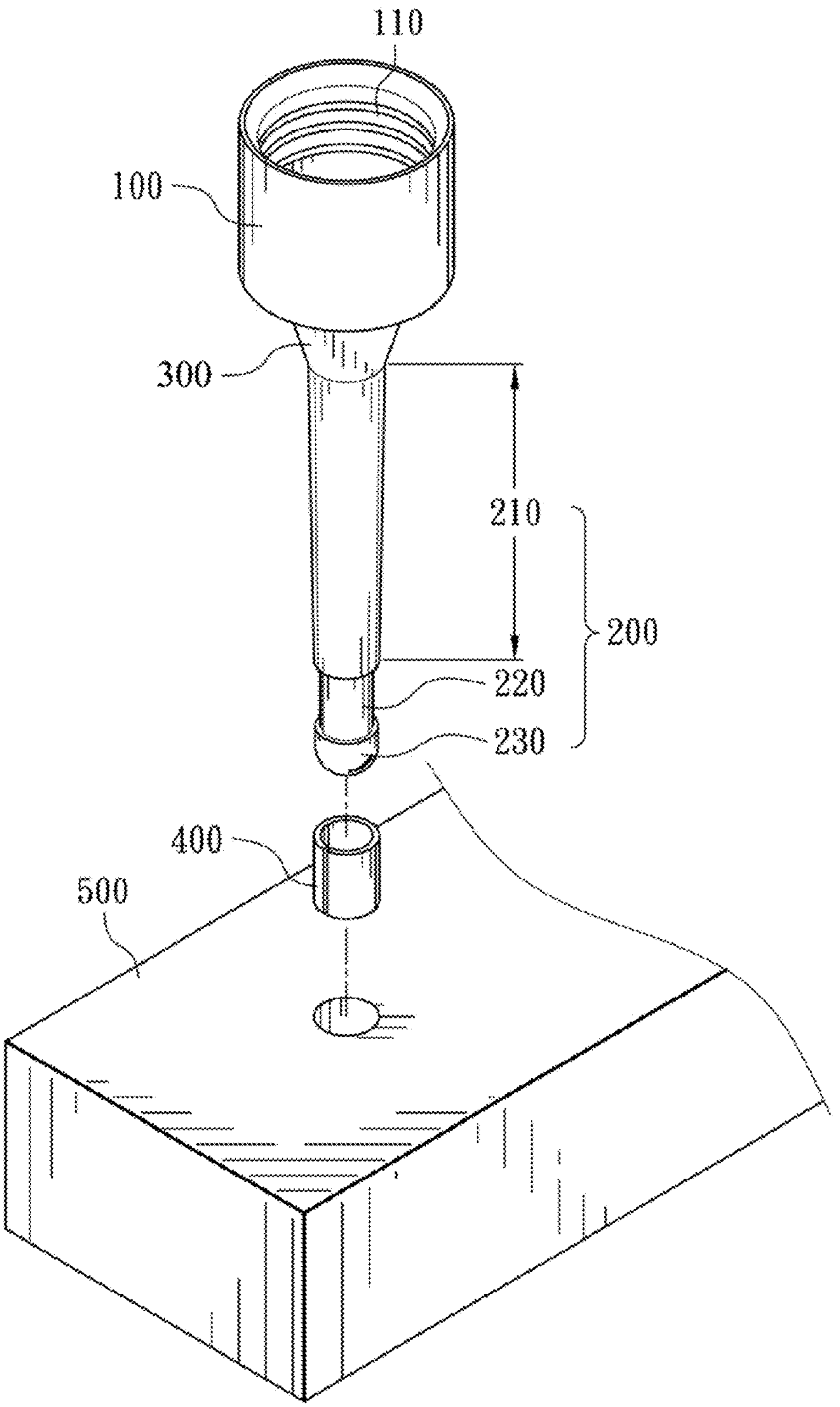
FIG. 2 is an exploded view of the reaction tube of FIG. 1.
Figure 3:
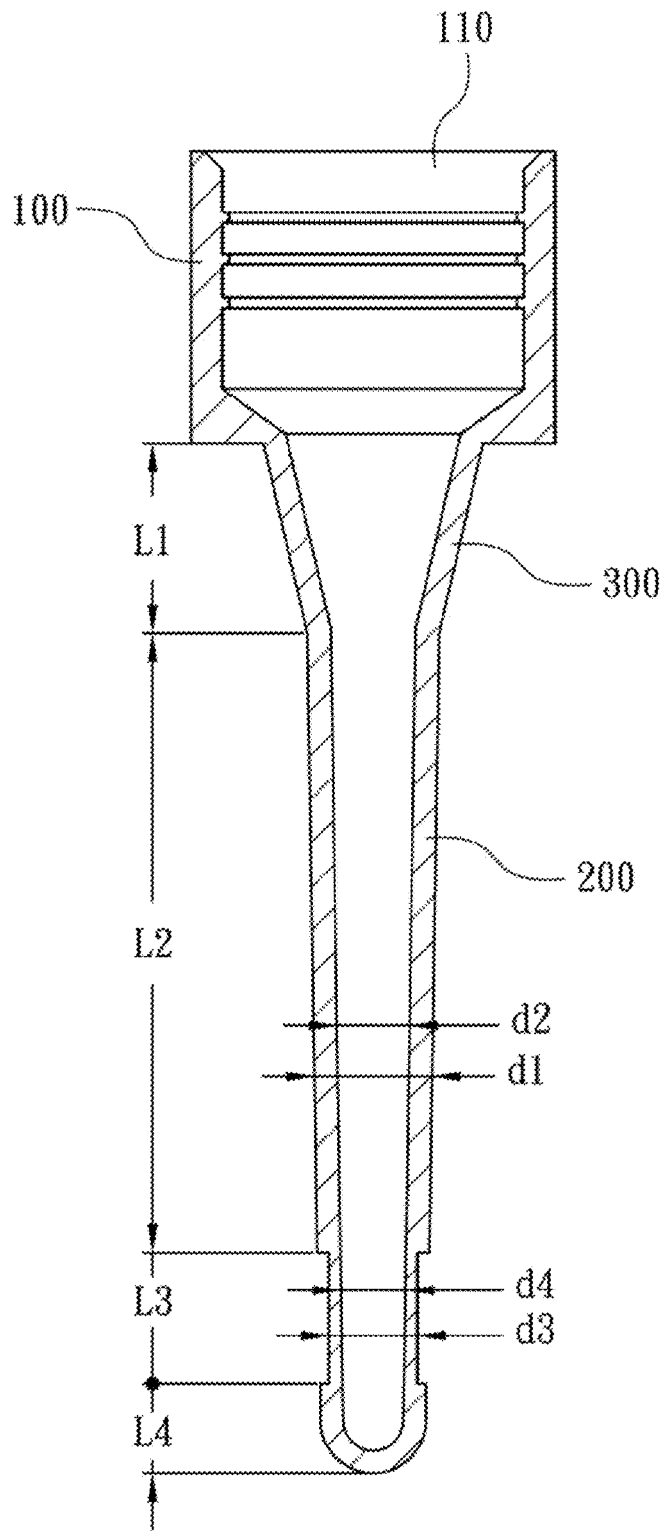
FIG. 3 is a cross-sectional view taken along line 4-4 of the reaction tube without the thermal conductor of FIG. 1.

FIG. 1 is a perspective view of a reaction tube according to an embodiment of the present disclosure FIG. 2 is an exploded view of the reaction tube of FIG. 1. FIG. 3 is a cross-sectional view taken along line 4-4 of the reaction tube without the thermal conductor of FIG. 1. The reaction tube is provided for performing an isothermal polymerase chain reaction therein and includes an upper section 100, a lower capillary section 200, a linkage 300 between the upper section 100 and the lower capillary section 200, and a thermal conductor 400. The lower capillary section 200 has an annealing portion 210, an annular heating groove 220, and a close end 230. The annealing portion 210 is tubular-shaped, and a vertical length L2 between two ends of the annealing portion 210 ranges from 13.5 mm to 14.5 mm. The annealing portion 210 is connected with the linkage 300, and the annular heating groove 220 is connected with the annealing portion 210. The close end 230 is connected with the annular heating groove 220. In addition, the upper section 100 further includes an opening 110 opposing the close end 230 for loading samples such as PCR reagents into the reaction tube to perform PCR therein. The linkage 300 is cone-shaped, and a vertical length L1 between two ends of the linkage 300 ranges from 4 mm to 5 mm. Plus, a vertical length L4 between two ends of the close end 230 ranges from 0.5 mm to 2.5 mm.

Furthermore, the thermal conductor 400 tightly embraces the annular heating groove 220 of the lower capillary section 200 for conducting heat to the lower capillary section 200 evenly from a heating source 500, where the thermal conductor 400 is received by the annular heating groove 220. Moreover, an outer diameter d1 of the annealing portion 210 is greater than an outer diameter d3 of the annular heating groove 220; the outer diameter d1 of the annealing portion 210 ranges from 2.95 mm to 3.1 mm, whereas the outer diameter d3 of the annular heating groove 220 ranges from 2.35 mm to 2.5 mm. Besides, the annular heating groove 220 is tubular-shaped, and a vertical length L3 between two ends of the annular heating groove 220 ranges from 2.8 mm to 3.2 mm. An inner diameter d2 of the annealing portion 210 is substantially equal to an inner diameter d4 of the annular heating groove 220 which ranges from 1.95 mm to 2.1 mm.

The aforementioned thermal conductor 400 may be clip-shaped or sleeve-shaped, and the thermal conductor 400 can be made of various thermal conductive materials like metal, such as iron, copper, etc.

Figure 4:
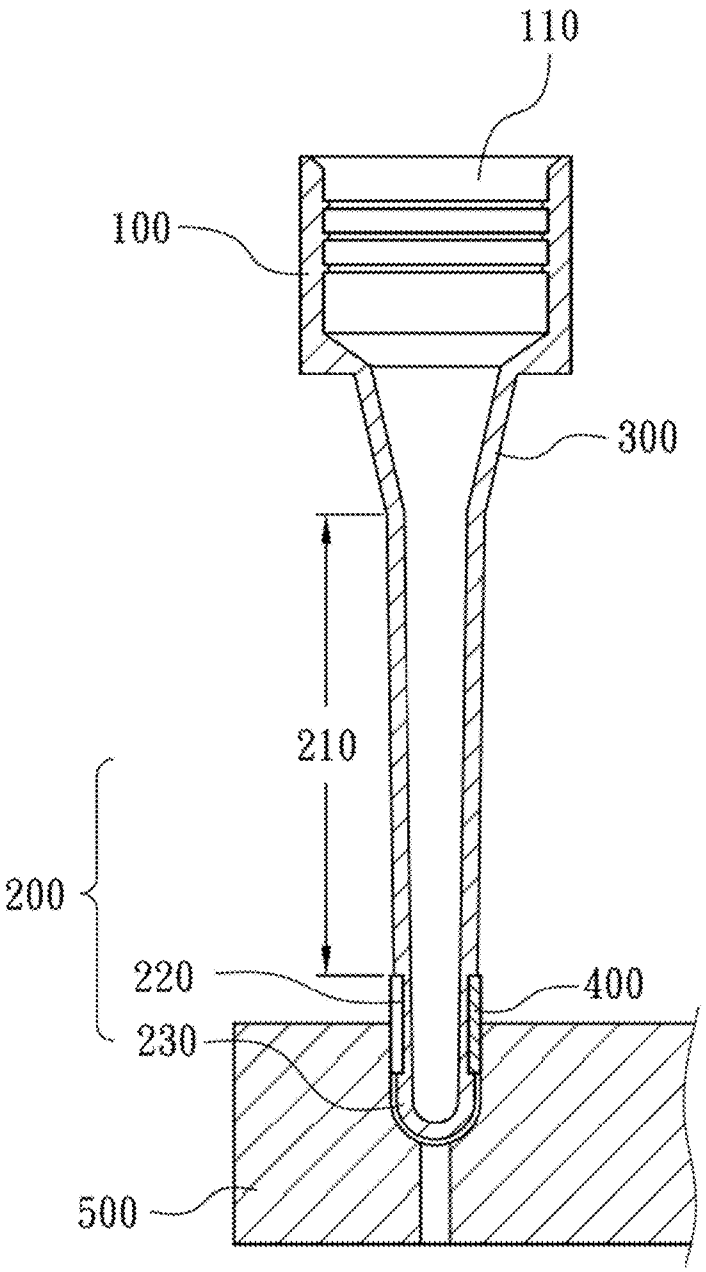
FIG. 4 is a cross-sectional view taken along line 4-4 of the reaction tube of FIG. 1.
Figure 5:
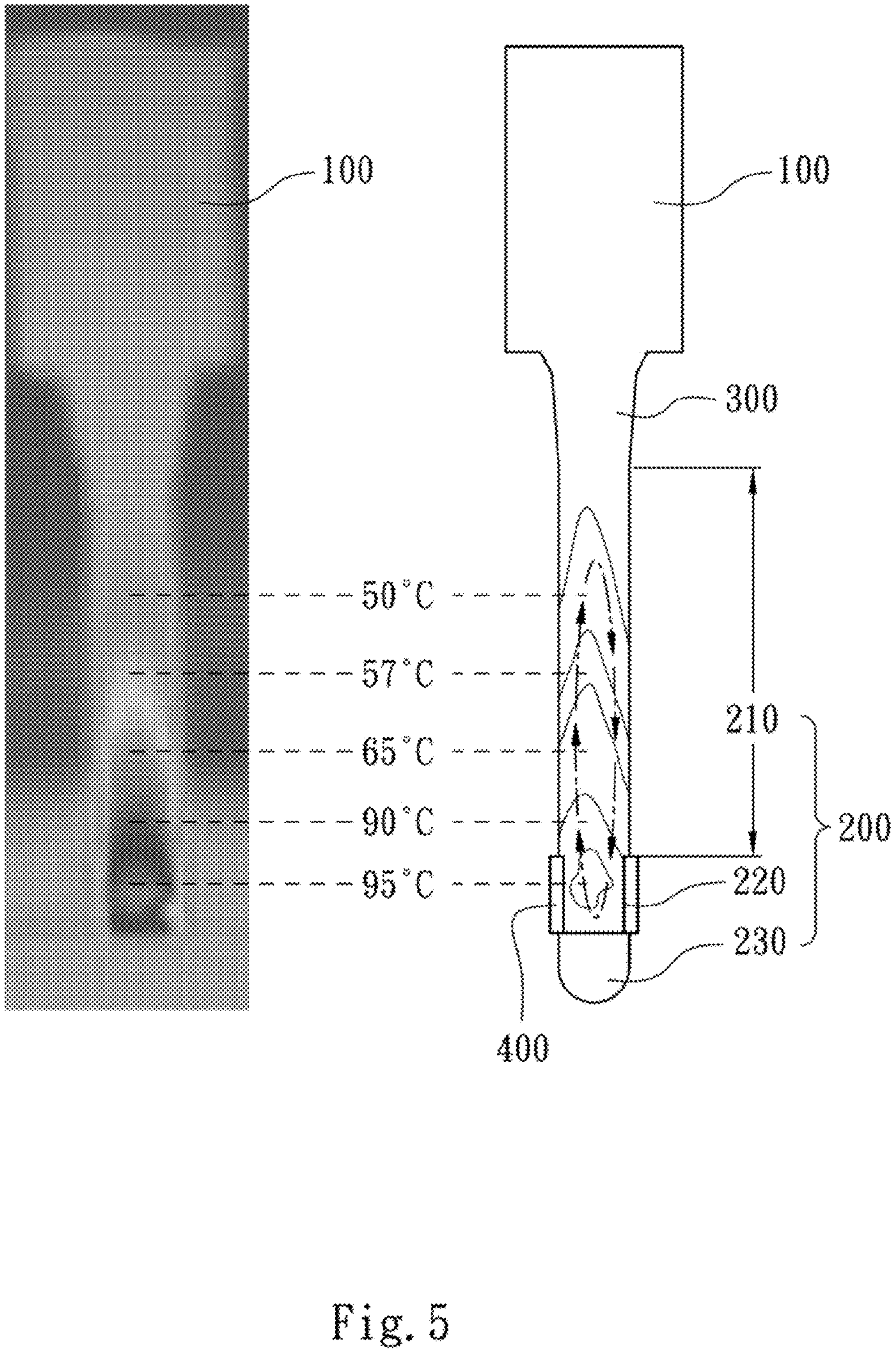
FIG. 5 is a schematic diagram of a temperature gradient associated with thermal convection while performing PCR in the reaction tube of the present disclosure, and a corresponding temperature profile thereof analyzed using an infrared thermometer.

FIG. 4 is a cross-sectional view taken along line 4-4 of the reaction tube of FIG. 1, and FIG. 5 is a schematic diagram of a temperature gradient associated with thermal convection while performing PCR in the reaction tube of the present disclosure, and a corresponding temperature profile thereof analyzed using an infrared thermometer. During operation, 40~60 μl PCR reagents, including pre-mixed buffer, dNTP, nucleic acid templates, primers or other chemicals associated in the PCR reaction, will be loaded into the opening 110 of the thermal conductor 400 of the reaction tube, which is contacted to the heating source 500, so that while the heating source 500 generates heat, the heat will be efficiently conducted to the annular heating groove 220 of the lower capillary section 200 via the thermal conductor 400. Further, because that the annular heating groove 220 is tightly and completely embraced by the thermal conductor 400, the heat generated from the heating source 500 will be evenly conducted to a region of the lower capillary section 200 of the reaction tube, that is, the region where the annular heating groove 220 locates.

Accordingly, a temperature gradient of PCR reagents contained in the reaction tube is performed along the lower capillary section 200, thereby generating thermal convection.

PCR cycles may then be performed by utilizing such a temperature gradient. First, the reaction of the PCR reagents located around the annular heating groove 220 will be evenly heated to about 94-96° C. by conducting heat from the heating source 500 thereto via the thermal conductor 400, and the nucleic acid templates of the PCR reagents will start to be denatured. Then, these denatured nucleic acid templates will be driven to a relatively lower temperature region of the lower capillary section 200, namely the upper part of the annealing portion 210, due to the thermal convection and the temperature gradient. While these denatured nucleic acid templates, namely single-stranded nucleic acids, is flown to the relatively lower temperature region of about 50-65° C., the primers of the PCR reagent will be annealed to these templates, and then these primer-annealed templates will be flown to another region having relatively higher temperature, namely the lower region of the annealing portion 210 or around an interface of the annealing portion 210 and the annular heating groove 220, which is about 75-80° C., so that the single-stranded nucleic acids may be started to be synthesized into double-stranded ones, and thus amplifying the nucleic acid templates which were desired to be amplified. These aforementioned procedures of regular PCR reaction are routine for a person having ordinary skills in the art of genetics, so that the unnecessary details of regular PCR reaction are abbreviated. The aforementioned PCR reaction utilizing a temperature gradient and thermal convection is called the isothermal polymerase chain reaction.

By performing PCR in the reaction tube of the present disclosure, there was no need to repeatedly raise and reduce the temperature manually or automatically by a conventional PCR thermal cycler, and therefore devices designed for performing PCR could be much simpler than the conventional PCR apparatus. In addition, the time period of adjusting or witching the heating source to different temperatures in conventional PCR thermal cyclers can also be omitted, and therefore significantly enhancing the efficiency of nucleic acid amplification.

Importantly, regarding to conventional PCR reaction tubes, while performing PCR without using a heat conductor like the thermal conductor 400 of the present disclosure to evenly conduct heat to the PCR reaction tube, the heat generated by heating devices will not be concentrated at the region desired to be heated, and the heat will be widely dispersed and consumed, the temperature gradient as well as the thermal convection will be disturbed, so that the whole efficiency of the PCR performed in the reaction tube will be strongly reduced in consequence.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

What is claimed is:

1. A reaction tube, comprising:

an upper section for receiving a reagent;

a lower capillary section for performing an isothermal polymerase chain reaction therein, having:

an annealing portion;

an annular heating groove connected with the annealing portion and located in a bottom part of the lower capillary section, wherein an outer diameter of the annealing portion is greater than an outer diameter of the annular heating groove; and a closed end connected with the annular heating groove;

a linkage connecting the upper section and the lower capillary section, wherein the annealing portion is connected with the linkage; and a thermal conductor tightly embracing the annular heating groove of the lower capillary section for conducting heat thereto from a heating source, wherein the thermal conductor is received by the annular heating groove;

wherein a heat generated from the heating source will be evenly conducted to the annular heating groove of the lower capillary section of the reaction tube, and the lower capillary section is only heated by the heat received at the annular heating groove;

whereby a temperature gradient involving a reduction of temperature from the bottom part of the lower capillary section to a top part the lower capillary section is then provided in order to perform a thermal convection, hence the thermal convection results in three events, (i) denaturation, (ii) annealing and (iii) extension, occurring repeatedly in different regions of a PCR sample, thereby performing the isothermal polymerase chain reaction in the lower capillary section.

2. The reaction tube of claim 1, wherein the thermal conductor is clip-shaped or sleeve-shaped.

3. The reaction tube of claim 1, wherein the thermal conductor is made of metal.

4. The reaction tube of claim 3, wherein the thermal conductor is made of iron or copper.

5. The reaction tube of claim 1, wherein the linkage is cone-shaped, and a vertical length between two ends of the linkage ranges from 4 mm to 5 mm.

6. The reaction tube of claim 1, wherein the annealing portion is tubular-shaped, and a vertical length between two ends of the annealing portion ranges from 13.5 mm to 14.5 mm.

7. The action tube of claim 6, wherein an inner diameter of the annealing portion ranges from 1.95 mm to 2.1 mm.

8. The reaction tube of claim 6, wherein the outer diameter of the annealing portion ranges from 2.95 mm to 3.1 mm.

9. The reaction tube of claim 1, wherein the annular heating groove is tubular-shaped, and a vertical length between two ends of the annular heating groove ranges from 2.8 mm to 3.2 mm.

10. The reaction tube of claim 9, wherein an inner diameter of the annular heating groove ranges from 1.95 mm to 2.1 mm.

11. The reaction tube of claim 9, wherein the outer diameter of the annular heating groove ranges from 2.35 mm to 2.5 mm.

12. The reaction tube of claim 1, wherein an inner diameter of the annealing portion is equal to an inner diameter of the annular heating groove.

13. The reaction tube of claim 1, wherein a vertical length between two ends of the closed end ranges from 0.5 mm to 2.5 mm.

* * * * *